(12) United States Patent
Robertson

(10) Patent No.: US 6,758,955 B2
(45) Date of Patent: Jul. 6, 2004

(54) METHODS FOR DETERMINATION OF ADDITIVE CONCENTRATION IN METAL PLATING BATHS

(75) Inventor: Peter M. Robertson, Winkel (CH)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/313,801

(22) Filed: Dec. 6, 2002

(65) Prior Publication Data

US 2004/0108214 A1 Jun. 10, 2004

(51) Int. Cl.⁷ .............................................. G01N 27/26
(52) U.S. Cl. ...................................... 205/81; 205/775
(58) Field of Search .................................. 205/81, 775

(56) References Cited

U.S. PATENT DOCUMENTS 6,280,602 B1 * 8/2001 Robertson ................... 205/775
6,592,737 B1 * 7/2003 Robertson ..................... 205/81

* cited by examiner

Primary Examiner—Robert R. Koehler
(74) Attorney, Agent, or Firm—Margaret Chappuis; Steven J. Hultquist

(57) ABSTRACT

The present invention relates to PCGA analytical procedure, in which each PCGA plating/measuring cycle is performed with the stripping and cleaning of test electrode immediately conducted before the equilibrium step, so as to use the metal plate layer formed during a previous plating/measuring cycle as a protective layer for the test electrode. The present invention also relates to PCGA calibration measurement protocol, in which both the calibration measurements and the sample measurement are conducted after a background measurement step.

10 Claims, 2 Drawing Sheets

US 6,758,955 B2

METHODS FOR DETERMINATION OF ADDITIVE CONCENTRATION IN METAL PLATING BATHS

BACKGROUND OF THE INVENTION

1. Field of the Invention

The present invention generally relates to determination of additives in metal plating baths, and more specifically to Pulsed Cyclic Galvanostatic Analysis (PCGA) of additive concentration in metal plating solutions.

2. Background of the Invention

The PCGA determination of additive concentration in metal plating baths involves the plating of the metal onto a test electrode from a sample metal plating solution.

Typically, the test electrode is cyclically plated and stripped multiple times for each quantity measured. Each plating/measurement cycle comprises the following steps:

Clean—the test electrode surface is thoroughly cleaned electrochemically or chemically using acid bath, followed by flushing with water or acid bath, Equilibrate—the test electrode and a reference electrode are exposed to the metal plating solution and allowed to reach an equilibrium state, Plate—metal element is electroplated onto the test electrode either at constant current, and electroplating potential between the test and reference electrodes is monitored and recorded, and Strip—the metal deposition is removed, e.g., by reversal of the plating current flow and/or exposure to an acid bath.

These four steps must be repeated for each plating/measuring cycle.

The plating is usually conducted after various sample solution preparation steps, in which the sample metal plating solution to be tested is conditioned for optimal measurement results. Such sample solution preparation steps include, for example, dilution of highly concentrated samples, addition of excessive suppressor for amplifying the accelerator responses, and introduction of complexing agent for forming colored complexes with certain additives in the sample solution.

For most PCGA analysis, the solution preparation steps are conducted right after the cleaning step, and before the test electrode is exposed to the conditioned metal plating solution for establishing the equilibrium state, as shown in FIG. 1A. In some instances, the solution preparation steps are conducted right after the stripping step of a previous plating-measuring cycle, either before or concurrently with the cleaning step, as shown in FIG. 1B.

During the solution preparation, the stripped or naked test electrode is either (1) exposed to the air, waiting to be cleaned, or (2) if already cleaned, it is usually submerged in a base solution, waiting to be contacted with the conditioned metal plating solution for establishing the equilibrium state.

In the former case, the naked test electrode is vulnerable to contamination while exposed to the air. In the latter case, since the time required for solution preparation varies significantly across different types of sample solutions, the duration when such test electrode is submerged in the base solution varies accordingly, which in effect changes the time required for the test electrode to reach equilibrium state.

It would therefore be a significant advance in the art, and is accordingly an object of the present invention, to minimize the variation of equilibration time between individual plating/stripping cycles and to protect the test electrode against potential contamination during the solution preparation step.

Moreover, conventional PCGA methods utilize calibration measurements for quick determination of the additive concentration in the sample metal plating solutions. The calibration measurements take place immediately after background measurement of the base solution, by adding the calibration solutions into the base solution, while the test electrode is continuously submerged in the base solution, without being exposed to the air at any time.

However, the sample measurement is carried out after previously tested solution (for example, calibration solution) is emptied from the analytical cell, and fresh base solution and sample solution are filled into the analytical cell.. During emptying and filling steps, the test electrode is exposed to the air, which causes the measured additive responses to appear "sluggish," and the time required for the test electrode to reach the equilibrium state becomes longer.

It is another object of the invention to provide new measurement protocols that minimize the differences between the calibration measurement conditions and the sample measurement conditions and thus increase the measurement accuracy.

Other objects and advantages will be more fully apparent from the ensuing disclosure and appended claims.

SUMMARY OF THE INVENTION

The present invention relates in one aspect to a method for measuring electroplating potentials of metal plating solutions, comprising the steps of:

(a) providing a measuring apparatus comprising a reference electrode, a test electrode, and electrical potential measuring circuitry electrically coupled between such reference electrode and the test electrode for measuring electrical potential therebetween, wherein the test electrode is coated by a metal layer previously deposited thereon;

(b) preparing a metal plating solution for measurement;

(c) stripping the metal layer from the test electrode and cleaning the test electrode;

(d) contacting the test electrode with the prepared metal plating solution, allowing the test electrode to come to an equilibrium state in the prepared metal plating solution;

(e) depositing metal onto the test electrode from the prepared metal plating solution, by electroplating at a constant or known current density; and (f) measuring and recording electroplating potential between the reference electrode and the test electrode during the electroplating process;

(g) optionally, repeating steps (b)–(f) for each metal plating solution to be measured.

The present invention in another aspect relates to a calibration method for determining concentration of a component of interest in a sample metal plating solution, comprising the steps of:

(a) preparing a base metal plating solution that contains all components of the sample metal plating solution, except the component of interest, or optionally to which has been added a known volume of the component of interest;

(b) preparing a plurality of calibration solutions, each of which contains the component of interest in a distinct, known concentration;

(c) performing a first background measurement, by measuring electroplating potential of a first volume of the base metal plating solution;

(d) successively adding the calibration solutions into the first volume of the base metal plating solution to form a base/calibration mixture, while measuring electroplating potentials of the base/calibration mixture after each addition of said calibration solutions;

(e) constructing a calibration curve, by plotting the electroplating potentials measured in steps (c) and (d) as a function of the concentration of the component of interest;

(f) performing a second background measurement, by measuring electroplating potential of a second volume of the base metal plating solution;

(g) adding the sample metal plating solution into the second volume of the base metal plating solution to form a base/sample mixture, and measuring electroplating potential of the base/sample mixture;

(h) determining the concentration of the component of interest in the sample metal plating solution, based on the calibration curve constructed in step (e) and the electroplating potential measured in step (f) and (g).

The present invention in another aspect relates to a calibration method for determining concentration of a component of interest in a sample metal plating solution, comprising the steps of:

(a) preparing a base metal plating solution that contains all components of the sample metal plating solution, except the component of interest, or optionally to which has been added a known volume of the component of interest;

(b) preparing a single calibration solution, containing the component of interest in a distinct, known concentration, wherein the amount of concentration of component in the calibration solution is equal to a theoretical concentration of the component of interest in the sample metal plating solution;

(c) performing a first background measurement, by measuring electroplating potential of a first volume of the base metal plating solution;

(d) adding the calibration solution into the first volume of the base metal plating solution to form a base/calibration mixture, while measuring an electroplating potential of the base/calibration mixture;

(e) constructing a calibration curve, by plotting the electroplating potentials measured in steps (c) and (d) as a function of the concentration of the component of interest;

(f) performing a second background measurement, by measuring electroplating potential of a second volume of the base metal plating solution;

(g) adding the sample metal plating solution into the second volume of the base metal plating solution to form a base/sample mixture, and measuring electroplating potential of the base/sample mixture;

(i) determining the concentration of the component of interest in the sample metal plating solution, based on the calibration curve constructed in step (e) and the electroplating potential measured in step (f) and (g).

Additional aspects, features and embodiments of the invention will be more fully apparent from the ensuing disclosure and appended claims.

DETAILED DESCRIPTION OF THE INVENTION, AND PREFERRED EMBODIMENTS THEREOF

The present invention uses the metal layer, which is deposited onto the test electrode during a previous PCGA plating/measurement cycle, as a protective layer for the test electrode substrate.

Figure 1A:
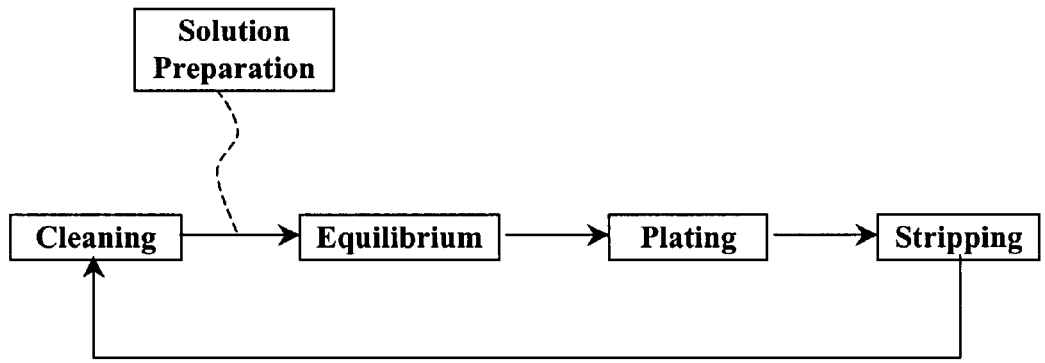
FIGS. 1A and 1B are diagrams showing the steps of conventional PCGA cycles.
Figure 1B:
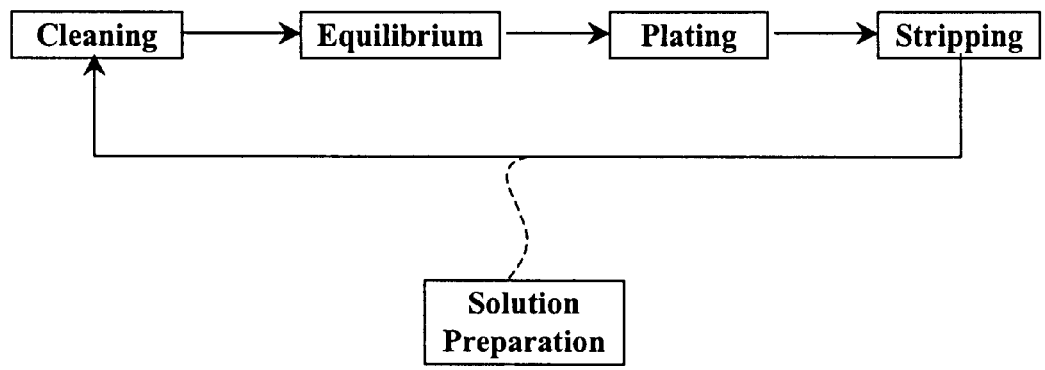

In a PCGA plating measurement cycle of the present invention, such metal layer is not immediately stripped off the test electrode after the plating and electropotential measurement step, as shown in the conventional PCGA plating/measurement cycles of FIGS. 1A and 1B. Instead, it is left on the test electrode when all the solution preparation steps for the next plating/measurement cycle are conducted, and stripping and cleaning of the test electrode are not performed until the sample solution to be tested has been properly conditioned and ready for plating. Then, the metal layer is stripped off the test electrode, and such test electrode is cleaned and subsequently inserted into the conditioned sample solution for reaching its equilibrium state before the plating starts.

Figure 2:
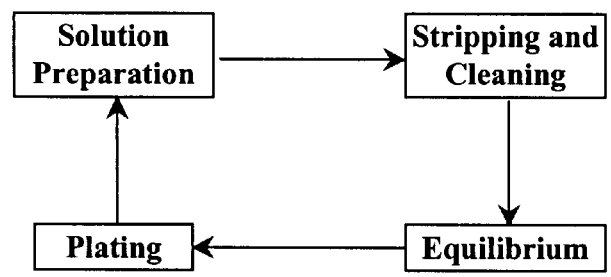
FIG. 2 is a diagram depicting the steps of a PCGA cycle according to one embodiment of the present invention.

FIG. 2 shows a typical PCGA plating/measurement cycle according to one embodiment of the present invention, which starts with (1) preparing/conditioning the sample plating solution, following by (2) stripping the metal layer off the test electrode and cleaning the test electrode for electro-potential measurement, (3) inserting the cleaned test electrode into the sample solution to establish an equilibrium state; and (4) electroplating metal onto the test electrode at a constant or known current density and measuring the electropotential between the test electrode and the reference electrode. Subsequent plating/measurement cycles can be carried out for additional sample solutions or calibration solutions, according to the four steps listed hereinabove.

During the stripping step, the electropotential of the test electrode (i.e., the stripping potential) is continuously monitored, and stripping is usually stopped as soon as the electropotential starts to run off anodically during or before the oxygen evolution.

By using the metal layer as a protective layer, the substrate of the test electrode is sheathed from potential contamination from the surrounding environment, while the test electrode is exposed to the atmosphere. The substrate of the test electrode is also protected against corrosion when such electrode is submerged in the base solution before preparation/condition of the sample solution is completed. As a result, the accuracy of the measurement results is enhanced, and the useful life of the test electrode is extended.

More importantly, by stripping the test electrode and exposing the substrate thereof immediately before contacting such test electrode with the sample metal plating solution, variance of equilibrium time required for different sample metal plating solutions is minimized.

In another aspect of the present invention, a novel measurement protocol is designed for measuring additive concentration in a sample metal plating solution, based on calibration method.

As mentioned hereinabove, conventional PCGA calibration analysis conducted uses different measurement protocols for calibration measurements and sample measurement. Specifically, during the calibration measurements, a background measurement was carried out for the base solution before addition of calibration solutions, and the test electrode is continuously submerged in the base solution, without being exposed to the air. On the other hand, during the sample measurement, no background measurement is carried out before addition of the sample metal plating solution. Instead, analytical cell is emptied and cleaned, during which the test electrode is exposed to the air, and the base solution and sample solution are subsequently filled into the analytical cell for measurement. The exposure of the test electrode to air increases the risk of contamination as well as slows down the additive responses, and the difference in measurement conditions between the calibration measurements and the sample measurement reduces the accuracy of such PCGA calibration analysis.

The present invention solves the above problems by providing a new measurement protocol for PCGA calibration analysis, in which the calibration measurements and sample measurement are conducted following substantially the same procedures and under substantially the same measurement conditions.

Specifically, the PCGA calibration analysis of the present invention is conducted by the following steps:

(1) filling an analytical cell with a first volume of a base metal plating solution that contains all components of the sample metal plating solution, except the component of interest (for example, the suppressor, the accelerator, or the leveler). Optionally, the base solution is conditioned, by diluting it with deionized water, or by adding excessive and known amount of suppressor, etc.;

(2) performing a first background measurement, by carrying out one or more plating/measuring cycles in such base metal plating solution. Preferably, multiple plating/measuring cycles are carried out, and the electropotential measured for each cycle is averaged;

(3) successively adding calibration solutions into the base solution to form a base/calibration mixture, wherein each calibration solution contains the component of interest in a distinct, known concentration, and measuring the electropotential of such mixture after each addition of the calibration solutions;

(4) constructing a calibration curve or a calibration data set, based on the electropotentials measured for the calibration solutions;

(5) emptying the analytical cell and filling it with a second volume of a base metal plating solution;

(6) performing a second background measurement, by carrying out one or more plating/measuring cycles in such second volume of the base metal plating solution, as described hereinabove;

(7) transferring the sample metal plating solution into the analytical cell, to form a base/sample mixture, and measuring electroplating potential of the base/sample mixture; and (8) determining the concentration of the component of interest in the sample metal plating solution, based on the calibration curve or calibration data set, and the background and sample measurement results.

Step (3) above, may be modified such that only one calibration solution is added into the base solution to form a single base/calibration mixture. The calibration will then proceed with a background measurement followed by addition of a single calibration solution A two-point calibration curve or data set is then prepared and the electroplating potential of a second volume of the base metal plating solution and a base/sample mixture, is measured for determination of the concentration of the component of interest as outlined in steps (5)–(8) above.

The concentration of the component of interest in the single calibration solution is ideally an amount that will result in a calibration solution having a very similar concentration to that in the sample metal plating solution and may be based on a theoretical concentration of the component of interest in the sample metal plating solution, which is readily determined by one of ordinary skill in the art.

The addition of a background measurement step before the sample measurement minimizes the procedure difference and measurement conditions between the calibration measurement and the sample measurement to a point where only a single calibration point is useful in preparing a corresponding calibration curve. Such background measurement further stabilizes the system, and addition of the sample solution into such stabilized system not only replicates the way in which the calibration measurements are conducted, but also increases the reproducibility and reliability of the sample measurement.

EXAMPLE 1

An analyzer consisting of 4 digital burettes was programmed to perform the following measurement protocol for determining the suppressor concentration in a sample solution:

| FIL | C2 | C3 | Bsp | C2 | C3 | INs |
|-----|-----|-----|-----|-----|-----|-----|
| 10.0 | 0.5 | 2.0 | 1 | 0.5 | 2.0 | 10.0 |

Figure 3:
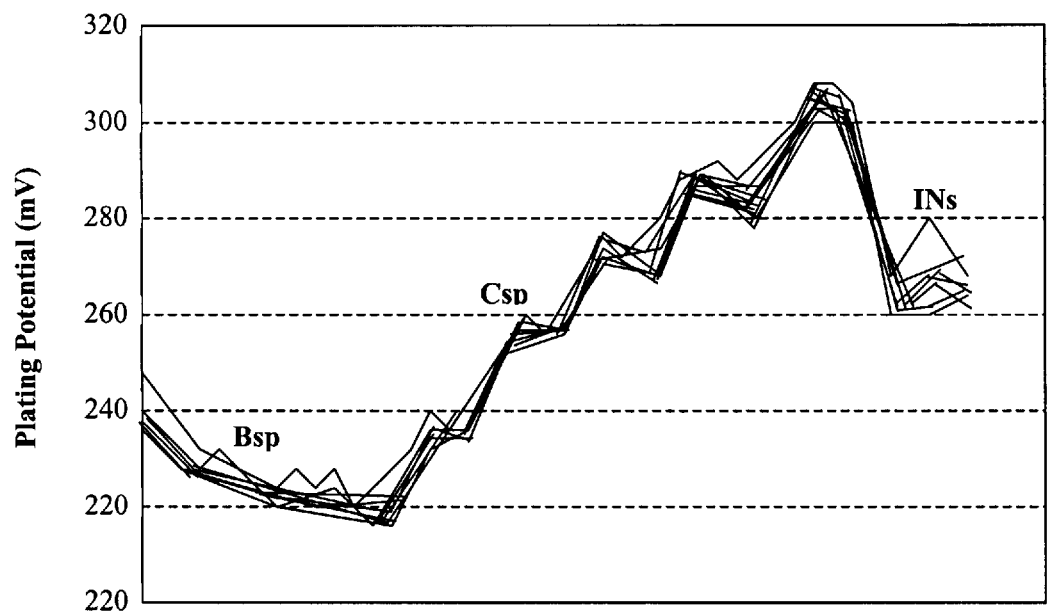
FIG. 3 is a graph plotting the electro-plating potentials measured for calibration solutions and a sample solution according to conventional PCGA measurement protocol.

FIG. 3 shows an electropotential response curve of a conventional PCGA calibration analysis, in which the background measurement (Bsp) is conducted only before the calibration measurements (Csp), and the sample measurement (INs) immediately follows the calibration measurement, without any background measurements.

Figure 4:
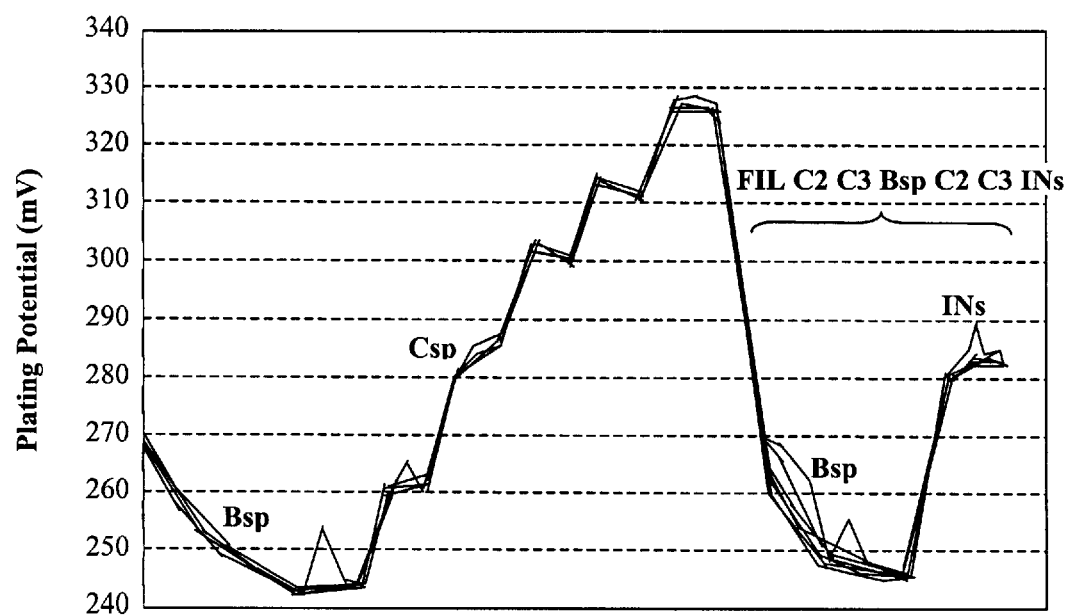
FIG. 4 is a graph plotting the electro-plating potentials measured for calibration solutions and the sample solution according to PCGA measurement protocol of the present invention.

FIG. 4 shows a response curve for the PCGA calibration analysis according to the present invention, in which an additional background measurement is conducted before the sample measurement.

The sample measurement results obtained without the additional background measurement (hereinafter "Bsp") tend to be higher than those obtained with the additional background measurement. For a sample solution that contains suppressor (LO) in a concentration of 10 mL/L, we obtained the following comparative measurement results:

| LO Concentration Measured with Bsp (mL/L): | LO Concentration Measured w/o Bsp (mL/L): |
|---|---|
| 10.4 | 13.8 |
| 11.0 | 14.2 |
| 10.2 | 17.2 |
| 12.8 | 16.1 |
| 10.8 | 17.3 |
| 12.6 | 13.6 |
| 10.6 | 14.1 |
| 10.4 | 14.3 |

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A method for measuring electroplating potentials of a metal plating solution comprising the steps of:

(a) providing a measuring apparatus comprising a reference electrode, a test electrode, and electrical potential measuring circuitry electrically coupled between said reference electrode and said test electrode for measuring electrical potential therebetween, wherein said test electrode is coated by a metal layer previously deposited thereon;

(b) preparing a metal plating solution for measurement;

(c) stripping the metal layer from the test electrode and cleaning said test electrode;

(d) contacting the test electrode with the prepared metal plating solution, allowing said test electrode to come to an equilibrium state in said prepared metal plating solution;

(e) depositing metal onto said test electrode from the prepared metal plating solution, by electroplating at a constant or known current density; and (f) measuring and recording electroplating potential between the reference electrode and the test electrode during the electroplating process;

(g) optionally, repeating steps (b)–(f) for each metal plating solution to be measured.

2. The method according to claim 1, wherein electropotential response of the metal plating solution is continuously monitored during the stripping of step (c).

3. The method of claim 2, wherein the stripping of step (c) is terminated when the electropotential shows anodic changes during or before oxygen evolution starts.

4. A calibration method for determining concentration of a component of interest in a sample metal plating solution, comprising the steps of:

(a) preparing a base metal plating solution that contains all components of the sample metal plating solution, except the component of interest, or optionally to which has been added a known volume of the component of interest;

(b) preparing a plurality of calibration solutions, each of which contains the component of interest in a distinct, known concentration;

(c) performing a first background measurement, by measuring electroplating potential of a first volume of the base metal plating solution;

(d) successively adding the calibration solutions into the first volume of the base metal plating solution to form a base/calibration mixture, while measuring electroplating potentials of the base/calibration mixture after each addition of said calibration solutions;

(e) constructing a calibration curve, by plotting the electroplating potentials measured in steps (c) and (d) as a function of the concentration of the component of interest;

(f) performing a second background measurement, by measuring electroplating potential of a second volume of the base metal plating solution;

(g) adding the sample metal plating solution into the second volume of the base metal plating solution to form a base/sample mixture, and measuring electroplating potential of the base/sample mixture;

(h) determining the concentration of the component of interest in the sample metal plating solution, based on the calibration curve constructed in step (e) and the electroplating potential measured in steps (f) and (g).

5. The method of claim 4, wherein the first and the second background measurements are conducted by performing multiple plating/measuring cycles and averaging the electroplating potential measured during each plating/measuring cycle.

6. The method of claim 4, wherein the component of interest is selected from the group consisting of suppressor, accelerator, and leveler.

7. A calibration method for determining concentration of a component of interest in a sample metal plating solution, comprising the steps of:

(a) preparing a base metal plating solution that contains all components of the sample metal plating solution, except the component of interest, or optionally to which has been added a known volume of the component of interest;

(b) preparing a single calibration solution, containing the component of interest in a distinct, known concentration, wherein the amount of concentration of component in the calibration solution is equal to a theoretical concentration of the component of interest in the sample metal plating solution;

(c) performing a first background measurement, by measuring electroplating potential of a first volume of the base metal plating solution;

(d) adding the calibration solution into the first volume of the base metal plating solution to form a base/calibration mixture, while measuring an electroplating potential of the base/calibration mixture;

(e) constructing a calibration curve, by plotting the electroplating potentials measured in steps (c) and (d) as a function of the concentration of the component of interest;

(f) performing a second background measurement, by measuring electroplating potential of a second volume of the base metal plating solution;

(g) adding the sample metal plating solution into the second volume of the base metal plating solution to form a base/sample mixture, and measuring electroplating potential of the base/sample mixture; and (h) determining the concentration of the component of interest in the sample metal plating solution, based on the calibration curve constructed in step (e) and the electroplating potential measured in step (f) and (g).

8. The method of claim 7, wherein the first and the second background measurements are conducted by performing multiple plating/measuring cycles and averaging the electroplating potential measured during each plating/measuring cycle.

9. The method of claim 7, wherein the component of interest is selected from the group consisting of suppressor, accelerator, and leveler.

10. The method of claim 7, wherein the one-point calibration generates a concentration of species being measured that matches closely the concentration measured in step (e) for the sample.

* * * * *